(12) United States Patent
Wang

(10) Patent No.: US 8,003,691 B2
(45) Date of Patent: Aug. 23, 2011

(54) ANTIVIRAL AND COMMA ANTIBACTERIAL PHARMACEUTICAL COMPOSITIONS OF CANTHARIDIC ANHYDRIDE AND METHOD OF PREPARATION THEREOF

(76) Inventor: Wei Wang, Min County (CN)

( * ) Notice: Subject to any disclaimer, the term of this patent is extended or adjusted under 35 U.S.C. 154(b) by 1785 days.

(21) Appl. No.: 10/496,561

(22) PCT Filed: Nov. 22, 2002

(86) PCT No.: PCT/CN02/00839
§ 371 (c)(1),
(2), (4) Date: May 21, 2004

(87) PCT Pub. No.: WO03/043623
PCT Pub. Date: May 30, 2003

(65) Prior Publication Data
US 2005/0070600 A1    Mar. 31, 2005

(30) Foreign Application Priority Data

Nov. 23, 2001 (CN) .................................. 01 1 40066

(51) Int. Cl.
*A01N 43/08* (2006.01)
*A61K 31/34* (2006.01)
(52) U.S. Cl. ...................................................... 514/468
(58) Field of Classification Search ................... 514/468
See application file for complete search history.

(56) References Cited

U.S. PATENT DOCUMENTS

| 4,678,664 A | * | 7/1987 | Schmolka | ....................... 424/65 |
| 6,110,679 A | | 8/2000 | Gotoh | |
| 6,114,348 A | * | 9/2000 | Weber et al. | .................. 514/299 |

FOREIGN PATENT DOCUMENTS

| CN | 1076111 | 9/1993 |
| CN | 1039588 | 8/1998 |
| CN | 1053338 | 6/2000 |
| CN | 1374310 | 10/2002 |

* cited by examiner

*Primary Examiner* — Yong Chong
(74) *Attorney, Agent, or Firm* — Kinney & Lange, P.A.

(57) ABSTRACT

The present invention relates to an antiviral and antibacterial pharmaceutical composition comprising cantharidic anhydride-essential oil preparation as effective ingredient and method for preparing thereof. The cantharidic anhydride-essential oil preparation is prepared by dissolving cantharidic anhydride at appropriate temperatures. The clinical trials demonstrate that the cantharidic anhydride-essential oil preparation is effective in the treatment of tuberculosis and various viruses infected diseases. Furthermore, a series of local formulations for external use for treatment and prevention of virus infections can be prepared from the said cantharidic anhydride-essential oil preparations.

21 Claims, No Drawings

ANTIVIRAL AND COMMA ANTIBACTERIAL PHARMACEUTICAL COMPOSITIONS OF CANTHARIDIC ANHYDRIDE AND METHOD OF PREPARATION THEREOF

CROSS REFERENCE TO RELATED APPLICATION(S)

This application is the National Stage of International Application No. PCT/CN02/00839 filed Nov. 22, 2002, which in turn claims the benefit of Chinese Application No. 01140066.8 filed Nov. 23, 2001.

FIELD OF THE INVENTION

The present invention provides antiviral and antibacterial pharmaceutical compositions of cantharidic anhydride and method for preparing thereof. More specifically, the invention provides antiviral and antibacterial pharmaceutical composition comprising cantharidic anhydride-essential oils preparation obtained by dissolving a cantharidic anhydride in essential oils or single constituent of essential oils as the effective ingredient and pharmaceutically acceptable vehicle or excipient. The clinical trials demonstrate that the pharmaceutical composition of present invention has excellent antibacterial and antiviral effect, particularly is effective in the treatment of the diseases infected by tubercule bacillus, staphylococcus, hepatitis virus, human immunodeficiency virus, influenza virus and rotavirus.

BACKGROUND OF THE INVENTION

Cantharidic anhydride (cantharidin, hydroxyl cantharidin) is an extremely poisonous substance extracted from the body of cantharis, cantharid and the like used in Chinese traditional medicine. Cantharis used as a drug was recorded to have anticancer effect in Chinese traditional medicine long ago. Classical cantharis plaster abroad is a blister formed by combining cantharis powder with bee wax, rosin, tallow etc. In the said plaster, the content of cantharis powder was 25%. According to solubility calculation and test observation, most of the cantharidic anhydride was not dissolved in the course of plaster preparation. Therefore this classical skin-irritating agent was only a manufactured product of cantharis powder. In recent years, especially after the discovery of that cantharidic anhydride can serve as anticancer drugs, studies on the pharmacology and clinical application of cantharidic anhydride grows rapidly. At present, cantharidic anhydride is obtained by the extraction of cantharis powder by organic solvents such as acetone, chloroform, ether and the like. In order to improve the yield of cantharidic anhydride from the conversion of magnesium cantharidate, people usually treated cantharis powder with concentrated hydrochloric acid before the extraction of cantharidic anhydride with organic solvents. The obtained cantharidic anhydride or hydroxyl cantharidic acid were then purified and made into pharmaceutical composition, for example, cantharidin tablet (Shanghai Q/WS-1-566-80) and cantharidin injection (Shanghai Q/WS-1-567-80) have been granted.

Recently it was found that cantharidic anhydride is an antiviral antibiotics. However, in human body and animal body, the said antibiotic effect of cantharidic anhydride is not obvious for non-fat-soluble species but is quite well for fat-soluble cantharidic anhydride (Journal of Nature, 1980, Vol. 3, 458 in Chinese), especially in the case of treating viral hepatitis. Preparations made from fat-soluble cantharidic anhydride are specific for such diseases. The present inventor has already disclosed the preparation of cantharidic anhydride in his early Chinese Patent Application (ZL 90106365.7). The preparation for the fat-soluble cantharidic anhydride pharmaceutical composition mainly comprises the following steps:

1. Firstly cantharis powder was soaked in organic solvents such as acetone, dichloromethane, trichloromethane and ether to extract the cantharidic oil and cantharidic anhydride in the cantharis powder into the organic phase.
2. After the cantharis powder was extracted with organic solvent, the residue was dried and then was soaked in solution of concentrate hydrochloric acid and acetone. Cantharidic acid is converted into cantharidic anhydride by concentrated hydrochloric acid and cantharidic anhydride is dissolved into organic phase by using acetone.
3. After the cantharidic anhydride and cantharidic oil in the above-mentioned organic phase were separated from the organic phase, petroleum ether was added to extract the cantharidic oil and thus the separation of cantharidic anhydride from cantharidic oil was achieved. The cantharidic anhydride obtained was combined with that separated in step 2.
4. A definite amount of cantharidic oil was added to refined fat and then a amount of cantharidic anhydride was added and the mixture was stirred and heated at 80-120° C. and finally intermediate product of fat soluble cantharidic anhydride was obtained.

The above-mentioned refined fat can be vegetable oils such as soy bean oil, corn oil vegetable seed oil, sun flower seed oil, sesame oil, cocoa butter and etc, or wool fat, tallow and the like.

The drugs containing fat solvent of cantharidic anhydride in the above-mentioned patent having good application value. However, the kind of formulation is limited by the nature of fat solvent and drug. For example, the preparatory technology and clinical operation of the injection made of fat solvent are not satisfied and convenient.

On the other hand, one third of the effective components of cantharidic anhydride in the body of cantharis exists in the form of salt of cantharidic acid. Therefore, in traditional Chinese medicine, the effect of medicine also comprises that from magnesium cantharidate when cantharis body was used as oral medication. Since salt of cantharidic acid is easily soluble in water, it would have advantage in preparatory technology and clinical operation. The method of extraction of magnesium cantharidate or salt of cantharidic acid from the body of cantharis and convertion them into purified product are quite complex and have a low yield. It is much more simple, economic, convenient to purify cantharidic anhydride first and then prepare pure salt of cantharidic acid through semi-synthesis. The existence of magnesium cantharidate and salt of cantharidic acid in natural cantharis body indicates that they exhibit biological antibiotic effect in the living cantharis body. Compared with cantharidic anhydride, they have the advantage of higher solubility in the body fluid of cantharis. Therefore salt of cantharidic acid has its own character to be an antibacterial and antiviral drug.

In addition, antiviral preparations containing salt of cantharidic acid are convenient to use, have antibiotic effect to many kinds of important bacteria and viruses and have applicability to wide range of medical practices. Several kinds of pharmaceutical preparations made of salt of cantharidic acid have similar antiviral effect as fat solvent-cantharidic anhydride. Pharmaceutical preparations made of salt of cantharidic acid can be used to certain fields of medical treatment and disease prevention that fat solvent-cantharidic anhydride can not be used.

The above-mentioned technology was disclosed in detail in another patent (ZL931101573) of the present inventor. However the preparatory technology for pharmaceutical preparations of salt of cantharidic acid is more complex and thus the manufacturing cost is higher.

Besides, as mentioned above, although cantharidic anhydride has antiviral effect, there is not any report regarding antibacterial effect for bacteria such as tubercule bacillus.

CONTENT OF THE INVENTION

The objective of the present invention is to provide an antiviral and antibacterial pharmaceutical composition. The pharmaceutical composition has excellent antibacterial and antiviral effect on pathogenic microorganisms such as tubercule bacillus, staphylococcus, hepatitis virus, human immunodeficiency virus (HIV), influenza virus and rotavirus. In addition, the present invention also provides an antiviral and antibacterial pharmaceutical composition for external local use. Preparations containing the pharmaceutical composition for local uses can widely be used for sterilization, sanitation and health care.

Another objective of the present invention is to provide method of preparation for the above-mentioned pharmaceutical composition.

To achieve above objective, the present invention provides an antiviral and antibacterial pharmaceutical composition comprising cantharidic anhydride as the effective ingredient and pharmaceutically acceptable vehicle or excipient, wherein cantharidic anhydride is dissolved in essential oils or single constituent of essential oils to form cantharidic anhydride-essential oils preparation, and the said cantharidic anhydride is in a range of 0.05%-0.7% by weight based on total weight of cantharidic anhydride-essential oils preparation.

Besides, the antiviral and antibacterial pharmaceutical composition of the present invention can also be used as drug for local use.

The pharmaceutical composition of the present invention comprises cantharidic anhydride-essential oils preparation and pharmaceutically acceptable vehicle or excipient, wherein the cantharidic anhydride is in a range of 0.05%-0.7% by weight based on total weight of cantharidic anhydride-essential oils preparation.

In addition, the pharmaceutical composition comprising cantharidic anhydride-essential oil has excellent antibacterial and antiviral effect on bacteria such as tubercule bacillus etc and various viruses.

In the pharmaceutical composition of the present invention, cantharidic anhydride is dissolved in essential oils or single constituent of essential oils to form cantharidic anhydride-essential oil preparation. The cantharidic anhydride has higher solubility in essential oil. For example, the solubility of cantharidic anhydride in water is approximately 0.003%; solubility in fat is 0.05% and solubility in essential oil can reach 0.7%. That is to say, concentration of cantharidic anhydride in essential oil can be 14 times larger than that in fat and more than 200 time larger than that in water.

Essential oil is also called as ethereal oil, volatile oil and aromatic oil. It is a fragrant, volatile vegetable oily liquid and is a product obtained by distillation of plant's flower, stem, leave, root or grass. It can also be obtained by the method of pressing, extraction or adsorption. There are many kinds of essential oil. Their main ingredients include terpenes, arenes, alcohols, aldehydes, ketones, ethers, esters, phenols and the like. For example, cinnamon oil contains 85%-90% cinnamaldehyde, small amount of cinnamic acid, benzoic acid, coumarin and the like, which have sweet smelling similar to cinnamic aldehyde having slight rosa banksiae fragrance and are used in foodstuff. Citronella oil mainly contains citronellal (35%-50%) and geraniol (35%-45%), which has smooth and sweet fragrance and slight lemon fragrance and are widely used in perfuming of soaps and articles for family uses. Essential oils are soluble in organic solvent such as ethanol. Most of them can not be dissolved in water or are slightly soluble in water.

Therefore, essential oils are used in the present invention for following characteristics: 1. cantharidic anhydride is soluble in essential oil so that the pharmaceutical composition can contain more cantharidic anhydride; 2. Most of essential oils are edible i.e. essential oils used in the present invention are conventionally used and edible, thus it will not have any adverse effect to human body; 3. Essential oils are soluble in alcohols such as ethanol and glycerol. Since ethanol and glycerol are soluble in water, it is possible to prepare water-soluble pharmaceutical composition for local use comprising cantharidic anhydride-essential oil preparation. Such pharmaceutical composition has more effectively antiviral and antibacterial effect.

In addition, essential oils with boiling point higher than 100° C. preferably higher than 160° C. are used in the present invention because the composition of cantharidic anhydride-essential oil is preferably be carried out under heating condition. Essential oil with higher boiling point will not volatilize during the course of preparation. When the preparation of cantharidic anhydride-essential oil composition is carried out at relatively lower temperature such as 50° C.-100° C., the essential oil, as far as the boiling point of is higher than 100° C., can be effectively used. Therefore, most of the conventional edible essential oils can be used to prepare the composition of cantharidic anhydride-essential oil according to the present invention.

The present invention also provides a method for preparing cantharidic anhydride pharmaceutical composition, comprising (1) adding cantharidic anhydride in an amount of 0.05%-0.7% by weight into refined essential oils or single constituent of essential oils, stirring at 40° C.-160° C. under atmospheric pressure and dissolving cantharidic anhydride in essential oils to obtain cantharidic anhydride-essential oil preparation;

(2) mixing the obtained cantharidic anhydride-essential oil preparation with pharmaceutically acceptable vehicle or excipient, and stirring homogeneously to obtain the desired pharmaceutical composition.

The cantharidic anhydride used in the present invention can be prepared according to the method described in Chinese Patent 90106365. In specifically, the preparation of cantharidic anhydride comprises following steps:

(1) Soaking cantharis powders in organic solvents to extract cantharidic anhydride into organic phase;

(2) Drying the said cantharis powder having extracted by organic solvent, Soaking dried powders in solution of concentrated hydrochloric acid and organic solvents, wherein cantharidic acid is converted into cantharidic anhydride by concentrated hydrochloric acid and cantharidic anhydride is dissolved into organic phase by using organic solvents;

(3) Separating cantharidic anhydride and cantharidic oil from organic phase of Step 1, adding petroleum ether to extract cantharidic oil, thereby separating cantharidic anhydride from cantharidic oil, and combining the cantharidic anhydride obtained with that separated in Step 2.

In the above-mentioned method of preparation for cantharidic anhydride, the organic solvent is selected from the group consisted of acetone, dichloromethane, trichloromethane, and ether.

Furthermore, in order to avoid the volatilization of effective ingredients of the cantharis, the cantharis powders are obtained by pulverizing and drying cantharis at a temperature of 55° C. or less.

According to the conventional method of preparation for the pharmaceutical composition, pharmaceutically acceptable vehicles or excipients are added to prepare antiviral and antibacterial pharmaceutical compositions of the present invention. Following routine pharmaceutical process, different forms of pharmaceutical compositions can be prepared by using pharmaceutically acceptable vehicles or excipients. The pharmaceutically acceptable vehicles or excipients are those conventionally used in the art and have not special limitation.

The present inventor has already carried out numerous studies regarding the antiviral and antibacterial effect of the cantharidic anhydride. The present inventor found found that culture medium containing 0.01 ppm cantharidic anhydride can completely deactivate tubercule bacillus and staphylococcus (the minimum concentration for virus deactivation of cantharidic anhydride is 0.000132 ppm). It was reported in literature that the minimum concentration for tubercule bacillus deactivation of streptomycin is 10 ppm, for rifampicin is 25 ppm. The above-mentioned test indicates that cantharidic anhydride has stronger antibacterial effect against tubercule bacillus and staphylococcus and thus has potential value of clinical use.

The cantharidic anhydride-essential oils preparation were used to treat pulmonary tuberculosis and tuberculous pleurisy end achieved much better clinical effect than those by combining administration of antitubercular agent such as isoniazid, streptomycin and rifampicin. In addition, cantharidic anhydride does not have adverse reaction to liver and bone marrow as other anti-tubercule bacillus drugs such as rifampicin did. The subjective symptom and blood sedimentation rate is recovered faster than those of antitubercular agents.

In addition, chloromycetin eye drops or erythromycin eye ointment are usually used in treating bacterial conjunctivitis. When eye drops or ointment comprising cantharidic anhydride (3-6 ppm) essential oil preparations of the present invention are used, the effective rate approaches 99%. The symptom mitigates within 1-2 hours after administration and heals in about 1-3 days. The cantharidic anhydride-essential oils preparation has much better effects than those of antibacterial chloromycetin eye drops or ointment.

When the cream comprising cantharidic anhydride-essential oil preparations of the present invention are applied to furuncle. The pain will be reduced after 2-3 hours and most of bouton disappear within 2-3 days.

Clinical tests have proved that the pharmaceutical composition comprising cantharidic anhydride-essential oil preparations has much improved clinical effect. Furthermore, it has lower dosage, convenient usage and without any adverse reaction.

In addition, essential oil is used as solvent of cantharidic anhydride in the present invention. Since the amount of essential oil used is not high and essential oils without adverse effect are selected, any side effects will not occur due to the addition of essential oil. For peppermint oil, and peppermint oil, the amount used is determined according to the need of production. In the preparations of the present invention, the amounts of sweet orange oil, spearmint oil, carvol, limonene used are far lower than that for food additives as prescribed by Committee for Food Code of United Nations.

Most of the essential oils are easier to be absorbed by skin than fats do. Therefore, the use of essential oils as solvents will enhance the permeability of medicament and thus improve their bioavailability. The medicament containing essential oil is easier to permeate into outer membrane of bacteria or virus thereby enhances the effect of cantharidic anhydride. Some essential oil will be excreted through lung. Therefore, the effect of cantharidic anhydride as an anti-pulmonary tuberculosis medicament will be promoted. Many kinds of essential oil are easily soluble in vegetable oil and can prepare extremely effective creams or ointments. Some essential oils are easily soluble in glycerol. In the present invention, Cantharidic anhydride is first dissolved in essential oil and then is made into preparations with glycerol. The said preparations are suitable for sexual organ use and becomes good preparation for controlling infections of hepatitis virus B and C and human immunodeficiency virus (HIV).

The present invention will be further described in detail by means of following examples. Of course, the present invention is not limited by these examples.

EXAMPLES

Example 1

Preparation of Cantharidic Anhydride-Essential Oil Preparation

Cantharidic anhydride-essential oil preparation of the present invention can be prepared according to the present inventor's early Chinese Patent (Application Number: 91110970.6). The process of preparation is as follows:

(1) Cantharis was pulverized in a pulverizer under 55° C. in dry state and dried cantharis powder was obtained.

(2) Cantharis powder was transferred to a soaking pot and was soaked with organic solvent such as acetone for 24 hrs or more. Repeated percolation for several times. The separated organic phase was charged into separator No. 1 and solid phase was put into lixiviating pot.

(3) Solid phase of cantharis powder residue was transferred to lixiviating pot was soaked with a solution of concentrated hydrochloric acid and acetone for 24 hrs or more and repeated percolation with acetone for many times. Organic phase was separated and was transferred to separator No. 2 while the residue was discharged.

(4) In separator No. 1, cantharidic anhydride and cantharidic oil in the organic phase mentioned in step (2) was separated from organic solvent acetone. Acetone was recovered while cantharidic anhydride and cantharidic oil was transferred to separator No. 3

(5) In the separator No. 3, petroleum ether was added to dissolve cantharidic oil. In the separator, cartharidic anhydride was separated from cantharidic oil. Cantharidic oil was discharged while cantharidic anhydride was transferred to refining pot.

(6) In the separator No. 2, organic phase was separated from inorganic phase (concentrated hydrochloric acid not reacted and salts formed after reaction). After inorganic phase was discharged, cantharidic anhydride was separated from organic solvent acetone and was transferred to refining pot.

(7) In the refining pot, cantharidic anhydride was washed repeatedly with petroleum ether, reheated to dissolve with solvent such as acetone and ethanol, cooled and crystallized to yield cantharidic anhydride crystal. Finally the said crystals were repeatedly heated to dissolve in appropriate amount of acetone. After cooling, crystallization was carried out 2 times or more, thus pure crystals of cantharidic anhydride with purity higher than 99% can be obtained. The said pure crystals were transferred to formulation kettle.

(8) Essential oils such as sweet orange oil, peppermint oil, spearmint oil or single constituent of essential oil such as limonene, carvol and the like were refined and sterilized. The refined essential oil was transferred to formulation kettle.

(9) In the formulation kettle, cantharidic anhydride and essential oil charged in a specified proportion were heated and stirred at 40° C.-180° C. and under atmosphere pressure to dissolve cantharidic anhydride in essential oil. When temperature reached about 90° C., cantharidic anhydride was quickly dissolved in essential oil, if further increasing temperature, the dissolution rate would not increased as the temperature. In the course of production, the most preferable dissolution temperature is in the range of 88-98° C. and the dissolution process can be completed within 30 minutes. The cantharidic anhydride-essential oil preparation containing 0.26%-0.7% cantharidic anhydride is obtained according to above steps 1-9.

To the cantharidic anhydride-essential oil preparation obtained in the above-mentioned process, a specified proportion of adjuvants (vehicle or excipient) were added to yield various pharmaceutical compositions containing cantharidic anhydride. The manufacturing process was carried out in formulation kettle. The preparing conditions and the process were further described by the following examples.

Example 2

Preparation of Cantharidic Anhydride Cream

The cantharidic anhydride cream was consisted of the following components:

| | |
|---|---|
| Cantharidic anhydride | 0.15 g-0.25 g |
| Essential oil | 40 g-50 g |
| Vegetable oil | 15 g-20 g |
| Other matrixes for ointment (stearic acid, octadecyl alchol, cetyl alcohol, bee wax, chlorinated vegetable oil and monostearyl-glyceride) | 15 g-25 g |
| Emulsifiers (tween, sapn, lecithin etc.) | 6-20 g |
| bacteriostatic agent | appropriate amount |
| water | balanced to total 250 g |

In the preparation kettle, dispersed emulsion made from distilled water and other ointment matrixes were melted in cartharidic anhydride-essential oil preparation prepared in example 1. The mixture was ground in colloid mill to yield emulsion. Upon cooling to room temperature, cantharidic anhydride cream was obtained.

Example 3

Preparation of Cantharidic Anhydride Enteric Coating Tablets

The cantharidic anhydride enteric coating tablets:

| | |
|---|---|
| Cantharidic anhydride | 0.06-0.1 g |
| Essential oil | 20-30 g |
| Vegetable oil | 8-10 g |
| Antioxidant | 0.06-0.09 g |
| Other adjuvants | appropriate amount |
| Total amount | 300 g (1000 tablets) |

In the preparation kettle, a specified amount of adjuvants was added and stirred homogeneously to prepare the tablets only adjuvants, then the cantharidic anhydride-essential preparation obtained in example 1 was homogeneously permeated into the tablets at 40° C.-60° C. Enteric coated to obtain the cantharidic anhydride enteric coating tablets.

Example 4

Preparation of Intravenous Injection Emulsion of Cantharidic Anhydride

| | |
|---|---|
| Pure cantharidic anhydride | 0.08-0.1 g |
| Refined single constituent of essential oil (such as limonene) | 16-20 g |
| Refined vegetable oil | 80-100 g |
| Emulsifier (lecithin for injection use etc.) | 6-12 g |
| Propanetriol | 0-20 g |
| Water (for injection use) | balanced to 1000 ml |

In the preparation kettle, a specified amount of purified water, emulsifier, glycerol were added under nitrogen atmosphere to make emulsion containing emulsifier. The cantharidic anhydride-essential oil preparation obtained in example 1 was added and was triturated by colloid mill and homogenizer to yield highly homogeneous emulsion. After sterilization, injection emulsion was obtained. The preparation process for injection emulsion is carried out under nitrogen atmosphere.

Example 5

Preparation of Cantharidic Anhydride Drop Pills

The cantharidic anhydride drop pill:

| | |
|---|---|
| Cantharidic anhydride | 0.06-0.1 g |
| Essential oil | 22-32 g |
| Vegetable oil | 10-12 g |
| Antioxidant | 0.06-0.09 g |
| Other adjuvants | appropriate amount |
| Total amount | 300 g (1000 drop pills) |

To the preparation kettle, vegetable oil and other adjuvants were added and then cantharidic anhydride-essential oil preparation prepared in example 1 was added and stirred at 66° C.-76° C. for 30-60 minutes to yield oily solution. Dropped to prepare pill, dried, and packed.

Beside Examples 1-5, the cantharidic anhydride-essential oil preparation obtained in Example 1 can also be used to make cantharidic anhydride injection, film coating, liniment, patch, rubber plaster, oral emulsion, capsule, enteric coating capsule, soft capsule, drop pill, honey boluses and the like.

In addition, the cantharidic anhydride-essential oil preparation obtained in Example 1 can also be used to local administration, for example in the form of sterilization and hygiene agent for treating or preventing bacterial or viral diseases.

For instance, the following preparations can be prepared:

1. Cantharidic Anhydride Ointment

| | |
|---|---|
| Cantharidic anhydride | 0.0003-0.03 g |
| Essential oil | 6-12 g |
| Fat | 460-520 g |
| Other ointment matrixes (such as stearic acid, stearyl alcohol, bee wax) | appropriate amount |
| Antioxidant | 0.2-8 g |
| Total | 600 g |

To the preparation kettle, sterilized fat and other auxiliary matrix were added and then cantharidic anhydride-essential oil preparation obtained in example 1 was added. Stirred continuously 1-2 hr at 66-76° C. until completely homogeneity. Filtered, cooled to room temperature, packed to obtain Cantharidic anhydride ointment. The ointment can be used to inhibit completely infections from burns, trauma and stitched wounds from surgical operations. It has excellent effect of easing pain. The pain can be alleviated even in the case of serious burn.

2. Cantharidic Anhydride Eye Ointment

| | |
|---|---|
| Cantharidic anhydride | 0.0002 g-0.02 g |
| Essential oil | 2-8 g |
| Fat | 460 g-520 g |
| Other matrixes (such as lanolin, bee wax, liquid paraffin) | appropriate amount |
| Antioxidant | 0.1 g-8 g |
| Final total amount | 600 g |

To the preparation kettle, cantharidic anhydride-essential oil obtained in Example 1 was added and the sterilized fat and other matrixes were added. The eye ointment was prepared by using the same method for preparing ointment. The said eye ointment had excellent effect for treating bacterial and viral infection of conjunctiva, which was better than that of the prior antibacterial and antiviral eye ointments.

3. Cantharidic Anhydride Emulsion for Special Use

Components:

| | |
|---|---|
| Cantharidic anhydride | 0.0003-0.03 g |
| Essential oil | 3-9 g |
| Antioxidant | 0.1-0.9 g |
| Glycerol (can replaced by propylene glycol, sorbitol, polyethylene glycol) | appropriate amount |
| Other adjuvants and perfume | appropriate amount |
| Distilled water | appropriate amount |
| Total | 900 g |

Glycerol and other adjuvants were added and then cantharidic anhydride-essential oil preparation obtained in Example 1 was added into the preparation kettle No. 10. Stirred continuously for 30-60 minutes at 66-76° C. and then distilled water and perfume were added and stirred again at 66-76° C. for 10-20 minutes. After cooled to room temperature, the desired slightly viscous emulsion for special use was obtained. The emulsion could be used for sexual organ to deactivate completely human immunodeficiency virus, hepatitis B virus, hepatitis C virus and various bacteria. It can prevent sexual infections. It also make patient feel comfortable and refreshing. Since the concentration of cantharidic anhydride exceeds the minimum deactivation concentration of virus over 10,000 times and cantharidic anhydride has no side effect to human organs, the emulsion is an ideal medicament for preventing sexual infectious diseases.

4. Cantharidic Anhydride Sterilized Wipes

| | |
|---|---|
| Cantharidic anhydride | 0.00036-0.036 g |
| Essential oil (such as phenethyl alcohol) | 3.6-9.6 g |
| Antioxidant | 2-12 g |
| Glycerol | appropriate amount |
| Other adjuvants and perfume | appropriate amount |
| Distilled water, skin-protecting solution of Chinese traditional medicine) | appropriate amount |
| total | 900 g |

To the preparation kettle, glycerol and other adjuvants were added and then cantharidic anhydride-essential oil preparation obtained in Example 1 was added. Stirred continuously for 30-60 minutes at 66-76° C., then distilled water and perfume were added and stirred again at 66-76° C. for 10-20 minutes. The drug solution for skin-protecting and disinfectant was obtained.

Wipes were soaked in the said drug solution according to specified weight proportion and the soaked drug solution was packed and sealed to obtain the final product.

The drug concentration of the wipes after the vaporization of water could reach over 30,000 times of the minimum viral deactivation concentration of cantharidic anhydride. The wipes can kill virus and bacteria on skin and on the superficial opening of wound of skin. Meantime, the wipes have the effect of wetting, protecting, and cleaning skin. In a trip or outdoors, it could be used to wash or clean face and hand. In case of trauma, it could be used to urgently wrap or cover the wound. It is an ideal article of sanitation and health care during trip.

Using the method similar to that above-mentioned, various local be prepared such as rubber plaster, aerosol, eye dropping oils, oils for burn, spray for burn, sterilization spray, suppositories, eye drops, ear drops, nose drops, sterilizing solution for oral cavity and the like.

Example 6

Clinical Experiments Concerning Tubercule Bacillus and Hepatitis Virus of the Pharmaceutical Composition Comprising Cantharidic Anhydride-Essential Oil Preparation The course of chemotherapeutic treatment for tuberculosis by combination of isoniazid etc has been prolonged to 18-24 months for "standard chemotherapeutic treatment" and 6-9 months for "short chemotherapeutic treatment" by the Chinese health administration. This suggests that the curing effect of the drug for treating tuberculosis has lowered. As a result, long time treatment is needed. The percentage of occurrence of side effect after above-mentioned long time combining administration has reached 70%-80%. In the period of administering drug of 1-2 year, patients were unable to take part in family and social labors mainly due to side effects of drug. However large amount of clinical experiments using pharmaceutical compositions comprising cantharidic anhydride-essential oil preparation as the main ingredient according to the present invention have ideal curative effects. For instance, when composition according to Example 2 was used to treat tuberculous pleuritis, time of auto-absorption rate of accumulated chest fluid, body temperature, blood sedimentation rate were all significantly better than that achieved by combination of isoniazid, streptomycin and rifampicin. In addition, the cantharidic anhydride preparations did not have any side effects. The specific clinical experiments were carried out according to the following processes.

1. The patients suffering with pulmonary tuberculosis in control group (I) were subjected to conventional combined treatment of isoniazid, streptomycin and rifampicin. The patients took drug continuously for 180 days and the results of clinical treatment were observed.
2. The patients suffering with pulmonary tuberculosis in control group (II) were administrated fat soluble cantharidic anhydride emulsion (preparation process was similar to Example 2 except essential oil was replaced by fat, the dosage of cantharidic anhydride in the pharmaceutical composition is identical with that of the following treatment group). The patients took drug continuously for 90 days and the results of clinical treatment were observed.
3. The patients suffering with pulmonary tuberculosis in treated group were administrated emulsion prepared in Example 2. The patients took drug continuously for 90 days and the results of clinical treatment were observed.

In addition, for control group (II) and treatment group, the emulsions were applied on the chest and back of the patients 3 times a day and 2 g of emulsion each time. The results obtained for the above treatments were illustrated in Tables 1-3.

TABLE 1

Comparison of three treatments for patients suffering from infiltrative pulmonary tuberculosis

| Group | No. of cases | The symptom such as anepithymia and hypodynamia disappearing (Average days) | The body temperature and blood sedimentation rate recovery (Av. Days) | Getting better shown by X-ray diagnosis (Av. Day) | recovery shown by X-ray diagnosis (Av. Days) | Remarks |
|---|---|---|---|---|---|---|
| Control group (I) | 36 | Over 60% patients did not recover due to side effects | 72.6 | 54.2 | 92.6 days 26 cases recovered, 10 cases can not recovered | Take drug continuously for 180 days |
| Control group (II) | 22 | 16.2 | 26.3 | 48.2 | 62.3 | Take drug continuously for 90 days |
| Treatment group | 26 | 11.6 | 19.8 | 19.8 | 43.3 | Take drug continuously for 90 days |

TABLE 2

Comparison of three treatments for patients suffering from tuberculous pleurisy

| Group | No. of cases | The symptom such as anepithymia and hypodynamia disappearing (Average days) | The body temperature and blood sedimentation rate recovery (Av. Days) | Accumlated chest fluid decreased shown by CT (Av. days) | Accumulated chest fluid completely absorbed shown by CT (Av. days) | Remarks |
|---|---|---|---|---|---|---|
| Control group (I) | 30 | Over 60% patients did not recover due to side effects | 59.6 | 42.3 | 66.6 | Take drug continuously for 90 days |
| Control group (II) | 20 | 13.2 | 24.6 | 24.6 | 38.2 | Take drug continuously for 90 days |
| Treatment group | 22 | 9.9 | 14.6 | 14.6 | 31.6 | Take drug continuously for 90 days |

TABLE 3

Comparison of occurrence of side effects for three treatments for patients suffering with infiltrative pulmonary tuberculosis and tuberculous pleurisy(3 months)

| Group | side effect | | | | No. of cases |
|---|---|---|---|---|---|
| | The symptom such as anepithymia, eating less and nausea (%) | Increase of liver toxic glutamate pyruvate transaminase (%) | Decrease of marrow and leucocyte (%) | Other side effects | |
| Control group (I) | 82.6 | 36.2 | 69.3 | 0 | 66 |
| Control group (II) | 0 | 0 | 0 | 0 | 42 |
| Treatment group | 0 | 0 | 0 | 0 | 48 |

In addition, clinical experiments were carried out on patients suffering hepatitis, especially those infected with hepatitis AE virus and hepatitis BC virus by using the pharmaceutical composition of the present invention. Three groups were carried out at same time.

1. In control group (I), decoction of traditional Chinese medicine was used,
2. In control group (II), fat-soluble cantharidic anhydride emulsion was used,
3. In treatment group, the emulsion comprising cantharidic anhydride prepared in Example 2 was used.

In the above control group (II) and treatment group, the same dosage and administrating methods were used. The results of three groups were illustrated in Table 4.

TABLE 4

Comparison of the curative effects on patients infected with hepatitis AE virus and hepatitis BC virus.

| group | | Item | | | No. of cases |
|---|---|---|---|---|---|
| | | Symtoms of anepithymia and hypodynamia getting better (Av. Days) | Symptoms completely disappear (Av. Days) | Jaundice Recovered shown by GPT, ALT analysis (Av. Days) | |
| Control group (I) | Hepatitis AE virus group | 6.8 | 31.8 | 36.3 | 16 |
| | Hepatitis BC virus group | 21.2 | 38.6 | 56.6 | 20 |
| Control group (II) | Hepatitis AE virus group | 3.6 | 12.6 | 21.1 | 20 |
| | Hepatitis BC virus group | 11.2 | 22.3 | 32.3 | 22 |
| Treatment group | Hepatitis AE virus group | 2.6 | 10.8 | 16.2 | 26 |
| | Hepatitis BC virus group | 8.3 | 19.6 | 28.2 | 26 |

In addition, results of clinical experiments obtained in treatments of acute viral conjunctivitis by using eye dropping oils of fat soluble cantharidic anhydride and cantharidic anhydride-essential oil of the present invention was illustrated in Table 5.

TABLE 5

Comparison of curative effects of eye dropping oils of fat soluble cantharidic anhydride and cantharidic anhydride-essential oil on acute viral conjunctivitis

| Group | Item | | P value |
|---|---|---|---|
| | Symptom of avoiding light, shedding tears and sand-rubbing lighten | Symptom of reddish swelling disappeared completely | |
| Treatment group using eye oil of fat soluble cantharidic anhydride | Av. 22 hrs | Av. 46.8 hrs | |
| Treatment group using eye oil of cantharidic arihydride-essential oil | Av. 32.2 minutes | Av. 26 hrs | < 0.01 |

Example 7

Antiviral Experiment Based on Tissue Culture Technique of Cantharidic Anhydride-Essential Oil Preparation Cantharidic anhydride antiviral test solution:

| | |
|---|---|
| Cantharidic anhydride | 0.1 g |
| Essential oil (completely soluble in glycerol) | 30 g |
| Glycerol | appropriate amount |
| Distilled water | appropriate amount |
| Total | 1000 g |

The contration of cantharidic anhydride of Cantharidic anhydride antiviral test solution was 100 ppm. According to the scheme of tissue culture, it is demanded that each group is cultured in different drug concentration and then diluted with water. The Cantharidic anhydride antiviral test solution was used as treatment group and cantharidic anhydride directly dissolved and diluted by water was used as control group. The experimental results are demonstrated in Table 6.

TABLE 6

Comparison of the antiviral experiment results on eight kinds of virus by cantharidic anhydride-essential oils preparation and aqueous solution of cantharidic anhydride

| Kind of virus | Minimum virus deactivation concentration of cantharidic anhydride for control group (ppm) | Minimum virus deactivation concentration of cantharidic anhydride for treatment group (ppm) |
|---|---|---|
| Adenovirus III | | 0.000163 |
| Cyncytial virus | | 0.000489 |
| Coxsackie B5 virus | | 0.000132 |
| Pollomyelitis virus | | 0.000256 |
| Herpes virus | | 0.000322 |
| Rotavirus | | 0.000169 |
| Hepatitis B virus | 0.0028 | |
| Human immunodeficiency virus | 0.0072 | |

In summary, the pharmaceutical compositions comprising cantharidic anhydride-essential oils preparation according to the present invention have broad spectrum of antiviral and antibacterial as shown by the result of a number of clinical experimental results. The pharmaceutical compositions according to the present invention have excellent curative effect on tuberculous disease, viral hepatitis, viral enteritis and the like.

What is claimed is:

1. An antiviral and antibacterial pharmaceutical composition comprising cantharidic anhydride as the effective ingredient and a pharmaceutically acceptable vehicle or excipient, wherein the cantharidic anhydride is dissolved in essential oils or a single constituent of essential oils at 40-160° C. to form a cantharidic anhydride-essential oils preparation, wherein the essential oils are selected from the group consisting of ethereal oil, volatile oil and aromatic oil, and the cantharidic anhydride is dissolved in a range of 0.05%-0.7% by weight based on a total weight of the cantharidic anhydride-essential oils preparation.

2. An antiviral and antibacterial pharmaceutical composition for external local use comprising cantharidic anhydride as the effective ingredient and a pharmaceutically acceptable vehicle or excipient, wherein the cantharidic anhydride is dissolved in essential oils or a single constituent of essential oils at 40-160° C. to form a cantharidic anhydride-essential oils preparation, wherein the essential oils are selected from the group consisting of ethereal oil, volatile oil and aromatic oil, and the cantharidic anhydride is dissolved in a range of 0.05%-0.7% by weight based on a total weight of the cantharidic anhydride-essential oils preparation.

3. A pharmaceutical composition against tubercule bacillus comprising cantharidic anhydride as the effective ingredient and a pharmaceutically acceptable vehicle or excipient, wherein the cantharidic anhydride is dissolved in essential oils or a single constituent of essential oils at 40-160° C. to form a cantharidic anhydride-essential oils preparation, wherein the essential oils are selected from the group consisting of ethereal oil, volatile oil and aromatic oil, and the cantharidic anhydride is dissolved in a range of 0.05%-0.7% by weight based on a total weight of the cantharidic anhydride-essential oils preparation.

4. A pharmaceutical composition against hepatitis virus and enteritis virus comprising cantharidic anhydride as the effective ingredient and a pharmaceutically acceptable vehicle or excipient, wherein the cantharidic anhydride is dissolved in essential oils or a single constituent of essential oils at 40-160° C. to form a cantharidic anhydride-essential oils preparation, wherein the essential oils are selected from the group consisting of ethereal oil, volatile oil and aromatic oil, and the cantharidic anhydride is dissolved in a range of 0.05%-0.7% by weight based on a total weight of the cantharidic anhydride-essential oils preparation.

5. The pharmaceutical composition according to claim 1, wherein the selected essential oils are edible essential oils.

6. A method for preparing the cantharidic anhydride pharmaceutical composition according to claim 1, comprising:
   (1) adding cantharidic anhydride in an amount of 0.05%-0.7% by weight into the essential oils or a single constituent of the essential oils, stiffing at 40-160° C. under atmospheric pressure, and dissolving the cantharidic anhydride in the essential oils to obtain the cantharidic anhydride-essential oils preparation;
   (2) mixing the obtained cantharidic anhydride-essential oils preparation with the pharmaceutically acceptable vehicle or excipient, and stiffing homogeneously to obtain the desired pharmaceutical composition.

7. The method according to claim 6, wherein the cantharidic anhydride is prepared according to the following steps:
   (1) Soaking cantharis powders in organic solvents to extract cantharidic anhydride into an organic phase;
   (2) Drying the cantharis powder extracted by organic solvent, soaking the dried powders in a solution of concentrated hydrochloric acid and organic solvents, wherein cantharidic acid is converted into cantharidic anhydride by the concentrated hydrochloric acid, and cantharidic anhydride is dissolved into the organic phase by using the organic solvents;
   (3) Separating the cantharidic anhydride and cantharidic oil from the organic phase of Step 1, adding petroleum ether to extract the cantharidic oil, thereby separating the cantharidic anhydride from the cantharidic oil, and combining the cantharidic anhydride obtained with that separated in Step 2.

8. The method according to claim 7, wherein the organic solvent is selected from the group consisted of acetone, dichloromethane, trichloromethane, and ether.

9. The method according to claim 7, wherein the cantharis powders are obtained by pulverizing and drying cantharis at a temperature of 55° C. or less.

10. The pharmaceutical composition according to claim 2, wherein the selected essential oils are edible essential oils.

11. A method for preparing the cantharidic anhydride pharmaceutical composition according to claim 2, comprising:
   (1) adding cantharidic anhydride in an amount of 0.05%-0.7% by weight into the essential oils or a single constituent of the essential oils, stiffing at 40-160° C. under atmospheric pressure, and dissolving cantharidic anhydride in the essential oils to obtain the cantharidic anhydride-essential oil preparation;
   (2) mixing the obtained cantharidic anhydride-essential oil preparation with the pharmaceutically acceptable vehicle or excipient, and stiffing homogeneously to obtain the desired pharmaceutical composition.

12. The method according to claim 11, wherein the organic solvent is selected from the group consisted of acetone, dichloromethane, trichloromethane, and ether.

13. The method according to claim 11, wherein the cantharis powders are obtained by pulverizing and drying cantharis at a temperature of 55° C. or less.

14. The pharmaceutical composition according to claim 3, wherein the selected essential oils are edible essential oils.

15. A method for preparing the cantharidic anhydride pharmaceutical composition according to claim 3, comprising:
(1) adding cantharidic anhydride in an amount of 0.05%-0.7% by weight into the essential oils or a single constituent of the essential oils, stiffing at 40-160° C. under atmospheric pressure, and dissolving cantharidic anhydride in the essential oils to obtain the cantharidic anhydride-essential oil preparation;
(2) mixing the obtained cantharidic anhydride-essential oil preparation with the pharmaceutically acceptable vehicle or excipient, and stiffing homogeneously to obtain the desired pharmaceutical composition.

16. The method according to claim 15, wherein the organic solvent is selected from the group consisted of acetone, dichloromethane, trichloromethane, and ether.

17. The method according to claim 15, wherein the cantharis powders are obtained by pulverizing and drying cantharis at a temperature of 55° C. or less.

18. The pharmaceutical composition according to claim 4, wherein the selected essential oils are edible essential oils.

19. A method for preparing the cantharidic anhydride pharmaceutical composition according to claim 4, comprising:
(1) adding cantharidic anhydride in an amount of 0.05%-0.7% by weight into the essential oils or a single constituent of the essential oils, stiffing at 40-160° C. under atmospheric pressure, and dissolving cantharidic anhydride in the essential oils to obtain the cantharidic anhydride-essential oil preparation;
(2) mixing the obtained cantharidic anhydride-essential oil preparation with the pharmaceutically acceptable vehicle or excipient, and stiffing homogeneously to obtain the desired pharmaceutical composition.

20. The method according to claim 19, wherein the organic solvent is selected from the group consisted of acetone, dichloromethane, trichloromethane, and ether.

21. The method according to claim 19, wherein the cantharis powders are obtained by pulverizing and drying cantharis at a temperature of 55° C. or less.

* * * * *

UNITED STATES PATENT AND TRADEMARK OFFICE
CERTIFICATE OF CORRECTION

| | |
|---|---|
| PATENT NO. | : 8,003,691 B2 |
| APPLICATION NO. | : 10/496561 |
| DATED | : August 23, 2011 |
| INVENTOR(S) | : Wei Wang |

It is certified that error appears in the above-identified patent and that said Letters Patent is hereby corrected as shown below:

Col. 5, Line 35
  Delete "end"
  Insert --and--

Col. 5, Line 42
  Delete "erythromycin"
  Insert --erythrocin--

Col. 16, Line 16
  Delete "stiffing"
  Insert --stirring--

Col. 16, Line 22
  Delete "stiffing"
  Insert --stirring--

Col. 16, Line 54
  Delete "stiffing"
  Insert --stirring--

Col. 16, Line 60
  Delete "stiffing"
  Insert --stirring--

Col. 17, Line 7
  Delete "stiffing"
  Insert --stirring--

Signed and Sealed this
Fourth Day of December, 2012

David J. Kappos
*Director of the United States Patent and Trademark Office*

CERTIFICATE OF CORRECTION (continued)
U.S. Pat. No. 8,003,691 B2

Col. 17, Line 12
  Delete "stiffing"
  Insert --stirring--

Col. 18, Line 5
  Delete "stiffing"
  Insert --stirring--

Col. 18, Line 11
  Delete "stiffing"
  Insert --stirring--